United States Patent
Cady et al.

(10) Patent No.: US 11,864,991 B2
(45) Date of Patent: Jan. 9, 2024

(54) INTRAOCULAR PSEUDOPHAKIC CONTACT LENS (IOPCL)-BASED TELESCOPIC APPROACH FOR TREATING AGE-RELATED MACULAR DEGENERATION (AMD) OR OTHER EYE DISORDERS

(71) Applicant: OnPoint Vision, Inc., Aliso Viejo, CA (US)

(72) Inventors: Kevin J. Cady, Laguna Hills, CA (US); Kevin L. Waltz, Indianapolis, IN (US)

(73) Assignee: OnPoint Vision, Inc., Aliso Viejo, CA (US)

( * ) Notice: Subject to any disclaimer, the term of this patent is extended or adjusted under 35 U.S.C. 154(b) by 209 days.

(21) Appl. No.: 17/332,533

(22) Filed: May 27, 2021

(65) Prior Publication Data

US 2022/0031448 A1    Feb. 3, 2022

Related U.S. Application Data

(60) Provisional application No. 63/057,738, filed on Jul. 28, 2020.

(51) Int. Cl.
    *A61F 2/16*    (2006.01)
(52) U.S. Cl.
    CPC .......... *A61F 2/1618* (2013.01); *A61F 2/1651* (2015.04); *A61F 2002/169* (2015.04); *A61F 2002/169053* (2015.04)
(58) Field of Classification Search
    CPC ................. A61F 2/1618; A61F 2/1651; A61F 2002/169; A61F 2002/169053;
    (Continued)

(56) References Cited

U.S. PATENT DOCUMENTS

| 4,124,905 A | 11/1978 | Clark |
| 5,133,747 A | 7/1992 | Feaster |

(Continued)

FOREIGN PATENT DOCUMENTS

| DE | 202013009162 U1 | 11/2013 |
| JP | 2004528065 A | 9/2004 |

(Continued)

OTHER PUBLICATIONS

Office Action dated Aug. 11, 2021 in connection with Australian Patent Application No. 2021200835, 2 pages.
(Continued)

*Primary Examiner* — Javier G Blanco

(57) ABSTRACT

A system includes an intraocular pseudophakic contact lens configured to be implanted in an eye and mounted on or attached to an artificial intraocular lens in the eye. The system also includes an external lens configured to be positioned in front of the eye. The intraocular pseudophakic contact lens and the external lens form a telescopic Galilean vision system. The external lens may include a spectacle lens or a contact lens. The intraocular pseudophakic contact lens may include an optical lens configured to provide a minus power optical magnification, and the external lens may be configured to provide a plus power optical magnification. The optical lens of the intraocular pseudophakic contact lens may include a central portion configured to provide a minus power optical magnification and an annular portion surrounding the central portion and configured to provide a different power optical magnification or no optical magnification.

20 Claims, 8 Drawing Sheets

(58) Field of Classification Search
CPC ............ A61F 2002/1681; A61F 2/1602; A61F 2/1613; A61F 2/1624
See application file for complete search history.

(56) References Cited

U.S. PATENT DOCUMENTS

| | | | |
|---|---|---|---|
| 5,814,103 | A | 9/1998 | Lipshitz et al. |
| 6,197,058 | B1 | 3/2001 | Portney |
| 6,827,738 | B2 | 12/2004 | Willis et al. |
| 7,008,449 | B2 | 3/2006 | Willis et al. |
| 7,186,266 | B2 | 3/2007 | Peyman |
| 7,220,278 | B2 | 5/2007 | Peyman |
| 9,808,339 | B2 | 11/2017 | Diaz et al. |
| 9,814,570 | B2 | 11/2017 | Robert et al. |
| 10,159,562 | B2 | 12/2018 | Cady |
| 10,299,910 | B2 | 5/2019 | Cady |
| 2002/0161436 | A1 | 10/2002 | Portney |
| 2004/0106993 | A1 | 6/2004 | Portney |
| 2004/0236422 | A1 | 11/2004 | Zhang et al. |
| 2006/0047339 | A1 | 3/2006 | Brown |
| 2006/0058874 | A1* | 3/2006 | Peli ................. A61F 2/1618 351/158 |
| 2006/0142856 | A1 | 6/2006 | Willis et al. |
| 2008/0312738 | A1 | 12/2008 | Wanders |
| 2009/0130176 | A1 | 5/2009 | Bossy-Nobs et al. |
| 2010/0121446 | A1 | 5/2010 | Bruce et al. |
| 2010/0131061 | A1* | 5/2010 | Callahan ............ A61F 2/1613 623/6.49 |
| 2011/0251686 | A1 | 10/2011 | Masket |
| 2013/0131796 | A1 | 5/2013 | Mirlay |
| 2013/0204364 | A1 | 8/2013 | Olson |
| 2014/0058507 | A1 | 2/2014 | Reich et al. |
| 2015/0342729 | A1 | 12/2015 | Kahook et al. |
| 2016/0081791 | A1 | 3/2016 | Cady |
| 2016/0317286 | A1 | 11/2016 | Brady et al. |
| 2017/0172733 | A1 | 6/2017 | Scharioth et al. |
| 2017/0296331 | A1* | 10/2017 | Werblin ............. A61F 2/1664 |
| 2017/0304045 | A1 | 10/2017 | Cady |
| 2019/0076237 | A1 | 3/2019 | Cady |
| 2019/0254808 | A1* | 8/2019 | Cady ..................... G02C 7/04 |
| 2019/0269555 | A1 | 9/2019 | Cady et al. |
| 2021/0186681 | A1 | 6/2021 | Qureshi et al. |

FOREIGN PATENT DOCUMENTS

| | | |
|---|---|---|
| JP | 2006511242 A | 4/2006 |
| JP | 2013528098 A | 7/2013 |
| JP | 2017528300 A | 9/2017 |
| JP | 2020526336 A | 8/2020 |
| KR | 101555298 B1 | 9/2015 |
| WO | 1991013597 A1 | 9/1991 |
| WO | 2008/094518 A1 | 8/2008 |
| WO | 2012054402 A2 | 4/2012 |
| WO | 2015/026226 A1 | 2/2015 |
| WO | 2021/126451 A1 | 6/2021 |

OTHER PUBLICATIONS

Examination Report No. 1 for Australian Patent Application No. AU2021245264 dated Sep. 20, 2022, 4 pages.
Examination Report No. 2 for Australian Patent Application No. AU2021245264 dated Nov. 23, 2022, 3 pages.
Decision to Grant a Patent for Japanese Patent Application No. 2021085035 dated Dec. 7, 2022, 4 pages.
Decision to Grant a Patent for Japanese Patent Application No. 2020501359 dated Nov. 29, 2022, 3 pages.
Written Decision on Registration for Korean Patent Application No. 10-2017-7008836 dated Aug. 19, 2022, 9 pages.
Japanese Patent Office, Office Action dated May 25, 2022 in connection with Japanese Patent Application No. 2021-085035, 4 pages.
Japanese Patent Office, Office Action dated Jul. 20, 2022 in connection with Japanese Patent Application No. 2020-501359, 4 pages.
International Search Report dated Feb. 17, 2021 in connection with International Patent Application No. PCT/US2020/61099, 1 page.
Notice of acceptance of patent application dated May 7, 2021 in connection with Australian Patent Application No. 2018301248, 3 pages.
Office Action dated Jul. 12, 2021 in connection with Australian Patent Application No. 2020239672, 4 pages.
European Search Report dated Jul. 16, 2021 in connection with European Patent Application No. 2116165.5, 5 pages.
Grant of Patent dated Jan. 17, 2022 in connection with Korean Patent Application No. 10-2021-7018671, 7 pages.
Office Action dated Jan. 3, 2022 in connection with U.S. Appl. No. 17/011,975, 20 pages.
Office Action dated Oct. 22, 2021 in connection with Canadian Patent Application No. 2,961,543, 5 pages.
European Search Report dated Sep. 2, 2021 in connection with European Patent Application No. 21 16 8724, 7 pages.
International Search Report and Written Opinion of the International Searching Authority dated Oct. 7, 2021 in connection with International Patent Application No. PCT/US2021/037911, 9 pages.
Office Action dated Aug. 24, 2021 in connection with Korean Patent Application No. 10-2021-7018671, 12 pages.
Office Action dated Sep. 24, 2021 in connection with Mexican Patent Application No. MX/a/2017/003760, 7 pages.

* cited by examiner ents used to describe the principles of the present
INTRAOCULAR PSEUDOPHAKIC CONTACT LENS (IOPCL)-BASED TELESCOPIC APPROACH FOR TREATING AGE-RELATED MACULAR DEGENERATION (AMD) OR OTHER EYE DISORDERS

CROSS-REFERENCE TO RELATED APPLICATION AND PRIORITY CLAIM

This application claims priority under 35 U.S.C. § 119(e) to U.S. Provisional Patent Application No. 63/057,738 filed on Jul. 28, 2020, which is hereby incorporated by reference in its entirety.

TECHNICAL FIELD

This disclosure relates generally to optical systems. More specifically, this disclosure relates to an intraocular pseudophakic contact lens (IOPCL)-based telescopic approach for treating age-related macular degeneration (AMD) or other eye disorders.

BACKGROUND

Age-related macular degeneration (AMD) causes deterioration of the macula in the retina of an eye. The retina is a paper-thin tissue at the back of the eye where light-sensitive cells send visual signals to the brain, and the macula supports finely-detailed vision. Sharp, clear, straight-ahead vision is centered in the macula, and damage to the macula results in central blind spots of various sizes and blurred or distorted central vision. Those affected by AMD find many daily activities, such as driving and reading, increasingly difficult and eventually impossible as the disease progresses. Common difficulties and symptoms of AMD include loss of ability to drive a car, loss of ability to read, distortion or loss of central vision, progressive decrease in contrast sensitivity, increase in glare and light sensitivity, need for increased illumination to read, and impaired depth perception.

AMD is the leading cause of visual impairment and irreversible vision loss in the United States. AMD is more prevalent among people 50 years of age or older, and it is one of the leading causes of legal blindness. As many as 15 million Americans currently have some type of AMD, including both early and intermediate stages. This number is expected to increase to nearly 22 million by 2050. Worldwide, it is estimated that more than 196 million people suffer from some level of AMD and that this number will increase to 288 million by 2040. Risk factors for developing AMD include positive family history, cigarette smoking, hyperopia, lightly-pigmented eye population, hypertension, and cardiovascular disease.

SUMMARY

This disclosure provides an intraocular pseudophakic contact lens (IOPCL)-based telescopic approach for treating age-related macular degeneration (AMD) or other eye disorders.

In a first embodiment, a system includes an intraocular pseudophakic contact lens configured to be implanted in an eye and mounted on or attached to an artificial intraocular lens in the eye. The system also includes an external lens configured to be positioned in front of the eye. The intraocular pseudophakic contact lens and the external lens form a telescopic Galilean vision system.

In a second embodiment, a method includes using an intraocular pseudophakic contact lens and an external lens to form a telescopic Galilean vision system. The intraocular pseudophakic contact lens is configured to be implanted in an eye and mounted on or attached to an artificial intraocular lens in the eye. The external lens is configured to be positioned in front of the eye.

In a third embodiment, a system includes an intraocular pseudophakic contact lens configured to be implanted in an eye and mounted on or attached to an artificial intraocular lens in the eye. The system also includes an external lens configured to be positioned in front of the eye, where the external lens includes a spectacle lens or a contact lens. The intraocular pseudophakic contact lens and the external lens form a telescopic Galilean vision system. The intraocular pseudophakic contact lens includes an optical lens and haptics extending radially from the optical lens and configured to be inserted under an anterior leaflet of a capsular wall in the eye. The optical lens of the intraocular pseudophakic contact lens is configured to provide a minus power optical magnification, and the external lens is configured to provide a plus power optical magnification. Posterior surfaces of the haptics include ridges configured to capture at least one edge of the artificial intraocular lens. The haptics are flexible such that outer portions of the haptics are configured to drive the ridges into the at least one edge of the artificial intraocular lens based on surface pressure from the anterior leaflet against the outer portions of the haptics.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

FIGS. 1 through 15, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

This disclosure relates to devices, systems, and techniques for treating age-related macular degeneration (AMD) or other types of eye disorders using a Galilean vision system. The Galilean vision system includes an intraocular pseudophakic contact lens (IOPCL) that can be mounted on, attached to, or otherwise secured to an artificial intraocular lens (IOL) for each of one or more eyes of a patient. The Galilean vision system also includes one or more external lenses, such as spectacles (eyeglasses) or contact lenses, with specially-designed power systems to magnify an image onto the macula(s) of the patient's eye(s). Among other things, the IOPCL-based Galilean magnification approach can be used to deliver a customized vision system to treat early and intermediate-stage AMD in pseudophakic patients. These patients may, for instance, have lost sufficient vision to support keeping their driving privileges. They may have also actually lost their drivers' licenses and/or the ability to read normal print.

Figure 1:
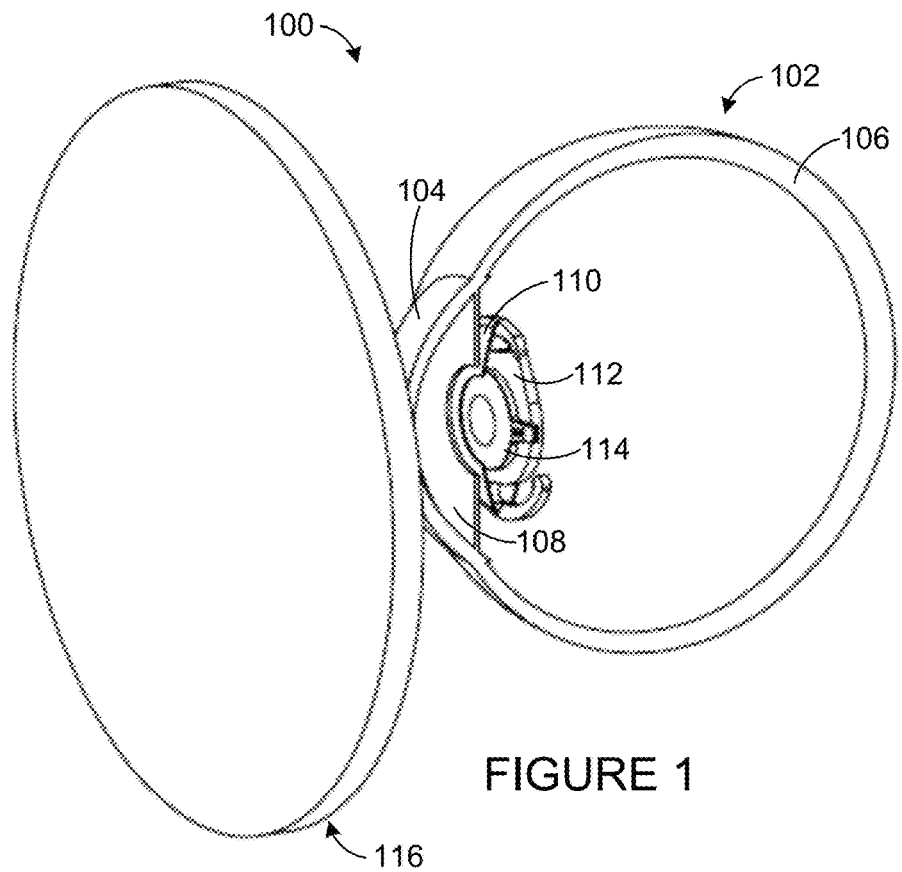
FIGS. 1 and 2 illustrate an example Galilean vision system according to this disclosure.
Figure 2:
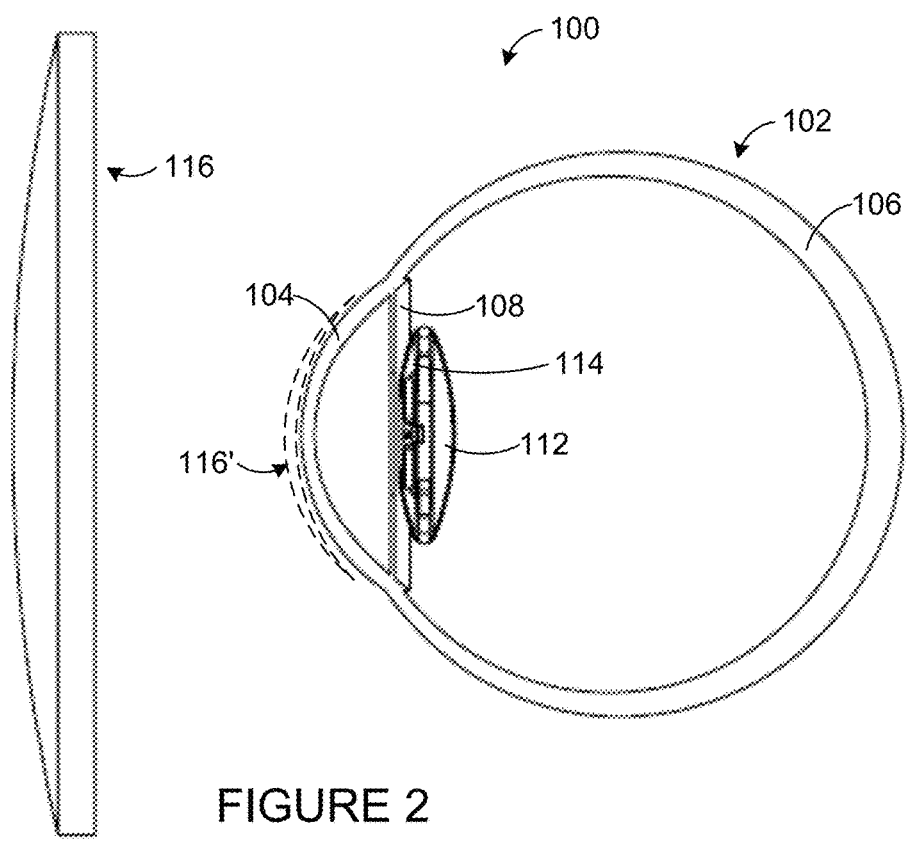

FIGS. 1 and 2 illustrate an example Galilean vision system 100 according to this disclosure. As shown in FIGS. 1 and 2, the Galilean vision system 100 is used in conjunction with an eye 102 of a patient. Depending on the circumstances, a single Galilean vision system 100 may be used with one eye 102 of the patient, or two Galilean vision systems 100 may be used with both eyes 102 of the patient. The eye 102 generally includes a cornea 104, a sclera 106, and an iris 108. The eye 102 itself is shown in cross-sectional form in FIG. 1 for ease of illustration and explanation. The cornea 104 represents the clear front portion of the eye 102 through which light passes to enter into the eye 102. The sclera 106 represents the tough outer white portion of the eye 102. The iris 108 represents the component of the eye 102 that controls the size of the eye's pupil to thereby control the amount of light from the cornea 104 that enters into the interior of the eye 102.

The eye 102 also includes a capsular bag 110, which typically holds the natural crystalline lens of the eye 102. However, in this example, the natural crystalline lens has been removed and replaced with an artificial intraocular lens (IOL) 112. The intraocular lens 112 generally includes an optical lens and one or more haptics. The optical lens of the intraocular lens 112 receives light entering the eye 102 and focuses the light onto the retina of the eye 102. The haptics of the intraocular lens 112 help to hold the intraocular lens 112 within the capsular bag 110 so that the optical lens of the intraocular lens 112 is in a desired position within the eye. An eye 102 in which the natural crystalline lens has been replaced with an artificial intraocular lens 112 is often referred to as a "pseudophakic" eye. Note that there are a wide variety of artificial intraocular lenses that may be used in a patient, and additional artificial intraocular lenses are sure to be developed in the future. The intraocular lens 112 shown here is for illustration only, and any other suitable artificial intraocular lens now known or later developed may be used in the Galilean vision system 100. Also, the intraocular lens 112 may be used here to provide any desired optical correction or other modification of light passing through the eye 102.

An intraocular pseudophakic contact lens (IOPCL) 114 has been placed on or otherwise in front of the intraocular lens 112 (possibly without touching the uveal tissue). The intraocular pseudophakic contact lens 114 represents an additional lens that can be mounted on, attached to, or otherwise secured to the intraocular lens 112. As shown here, the intraocular pseudophakic contact lens 114 may be placed on or in front of the anterior surface of the intraocular lens 112, meaning the front surface of the intraocular lens 112 with respect to the eye 102. Light enters through the cornea 104 and passes through the pupil before entering the intraocular pseudophakic contact lens 114, which modifies the light. The modified light then passes through the optical lens of the intraocular lens 112 and is again modified. The twice-modified light then travels through the remainder of the eye 102 to reach the retina at the back of the eye 102.

As described below, the intraocular pseudophakic contact lens 114 includes an optical lens and optionally a mechanism for securing the intraocular pseudophakic contact lens 114 to or against the intraocular lens 112. In some embodiments, for example, the intraocular pseudophakic contact lens 114 includes one or more haptics that extend a short distance and fit under an anterior leaflet of the capsular bag 110 in the eye 102. This allows the haptics to be captured and confined by the anterior leaflet and possibly attach to the capsular wall of the anterior leaflet via fibrosis or re-fibrosis. The anterior leaflet represents the outer portion of the front side of the capsular bag 110 that remains after an opening (referred to as a capsulorhexis) is formed in the capsular bag 110 so that the natural crystalline lens can be removed. The insertion of the haptics of the intraocular pseudophakic contact lens 114 under the anterior leaflet helps to secure the intraocular pseudophakic contact lens 114 in place. In some cases, the healing process in the eye 102 can cause fibrosis or re-fibrosis to occur, which could also attach the anterior leaflet to the haptics of the intraocular pseudophakic contact lens 114. In other embodiments, the intraocular pseudophakic contact lens 114 includes one or more pins that can pierce the lens material of the intraocular lens 112. In still other embodiments, the intraocular pseudophakic contact lens 114 may be designed to mate with or otherwise connect to one or more components of the intraocular lens 112 specifically designed for use with the intraocular pseudophakic contact lens 114. In general, any suitable mechanism(s) may be used to mount, attach, or otherwise secure the intraocular pseudophakic contact lens 114 in place relative to the intraocular lens 112.

An external lens 116 is positioned in front of the eye 102. In this example, the external lens 116 takes the form of a spectacle lens (such as an eyeglass lens) that may be held in place in front of the eye 102 (such as using a frame worn by a patient). However, the external lens 116 may also take other forms, such as a contact lens 116' that is worn over the cornea 104 of the eye 102. The external lens 116 and the intraocular pseudophakic contact lens 114 (with or without the intraocular lens 112) form the Galilean vision system 100. More specifically, the Galilean vision system 100 is formed using two high-power optics with opposite powers. The intraocular pseudophakic contact lens 114 includes a high minus power optical segment, which is implanted into the eye 102. The high minus power segment of the intraocular pseudophakic contact lens 114 creates a large hyperopic refractive error in a portion of the patient's field of view while preserving the patient's current distance visual field and peripheral acuity. In some embodiments, the high minus power segment of the intraocular pseudophakic contact lens 114 may act as the "eyepiece" for a Galilean telescope system.

To complete the Galilean telescope system, the external lens 116, such as a high plus power spectacle lens, contact lens, or other external lens, is placed in front of the eye 102.

The high plus power causes the external lens 116 to essentially act as the objective lens for the Galilean telescope system. The high plus power lens may be fabricated in any suitable manner. For example, in some cases, the high plus power lens can be created with a diffractive phase plate created by a specialty spectacle manufacturer to achieve a very high plus power while maintaining minimal weight and thickness. The use of specialized corrective eyewear can help to avoid problems experienced in prior approaches. Moreover, the use of specialized corrective eyewear can allow for subsequent adjustments of the magnification effect as a patient's eyesight gradually deteriorates over time due to AMD progression or other disorder. However, other techniques for fabricating the external lens 116 may be used.

Depending on the implementation, the intraocular pseudophakic contact lens 114 may be multi-focal and include a combination of lens powers, such as a high minus power optical segment and an optical segment with a different power or no power. This may allow for vision with and without the complete Galilean vision system 100 as needed. This means that, without the external lens 116 in place and with just the intraocular pseudophakic contact lens 114 in place, a patient may be able to enjoy the benefits of improved magnification, such as approximately 1.4-times to 1.6-times magnification. This level of magnification may be sufficient to allow a patient whose vision has decreased from a distance-corrected distance visual acuity (DCDVA) of 20/40 to a best-corrected distance visual acuity (BCDVA) of 20/60 to return to a BCDVA of approximately 20/40. This can be sufficient to read normal-sized print or to regain the patient's driver's license. With the external lens 116 in place along with the intraocular pseudophakic contact lens 114, the Galilean vision system 100 may achieve an even larger amount of magnification. Thus, in various approaches, patients may have the benefit of normal width and magnification of their visual fields (without the external lens 116 in place) and more magnification (with the external lens 116 in place).

While often described as being used to treat both eyes 102 of a patient, this is not necessarily required. For instance, a single eye 102 of a patient may be treated, and a contact lens, spectacle, or other external lens 116 may be used with that eye 102 to provide a Galilean telescope system for that eye 102. The other eye 102 of the patient may lack a contact lens, spectacle, or other external lens 116, or the other eye 102 may include a different contact lens, spectacle, or other external lens 116 (possibly a blank or non-corrective spectacle). The other eye 102 of the patient may or may not include an intraocular pseudophakic contact lens 114, and there is no requirement that the other eye 102 include the same type of intraocular pseudophakic contact lens 114. In general, the approaches described here can be easily customized to provide desired correction(s) of each patient's eye(s) 102 individually or collectively.

The desired optical powers of the intraocular pseudophakic contact lens 114 and the external lens 116 may be achieved in any suitable manner. For example, in some embodiments, the segment power of the intraocular pseudophakic contact lens 114 could be delivered in a central aperture or a dedicated segmented zone of varying power or shape on the posterior or anterior side of the optic in the intraocular pseudophakic contact lens 114. The external lens 116 may also have any suitable anterior and posterior surfaces that provide a desired optical power.

Although FIGS. 1 and 2 illustrate one example of a Galilean vision system 100, various changes may be made to FIGS. 1 and 2. For example, any suitable intraocular pseudophakic contact lens 114 (with or without an intraocular lens 112) and any suitable external lens 116 may be used to form the Galilean vision system 100.

Figure 3:
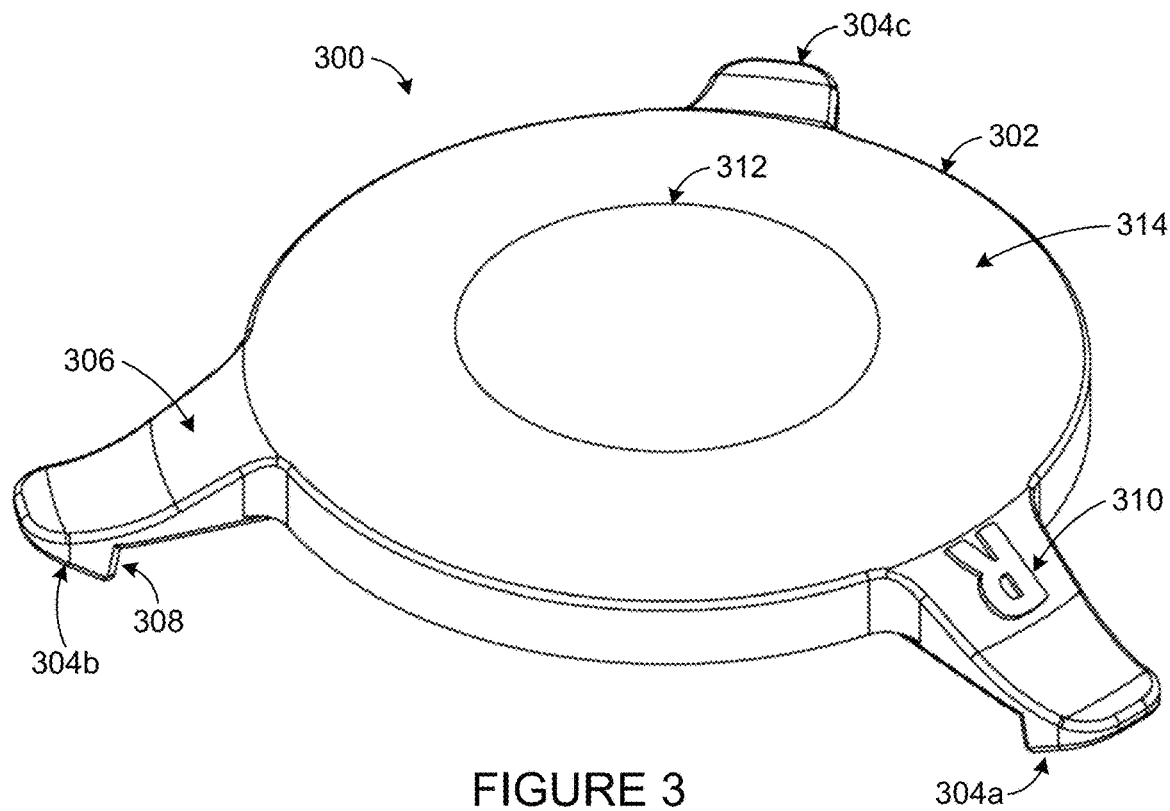
FIG. 3 illustrates a perspective view of an example intraocular pseudophakic contact lens for a Galilean vision system according to this disclosure.
Figure 4:
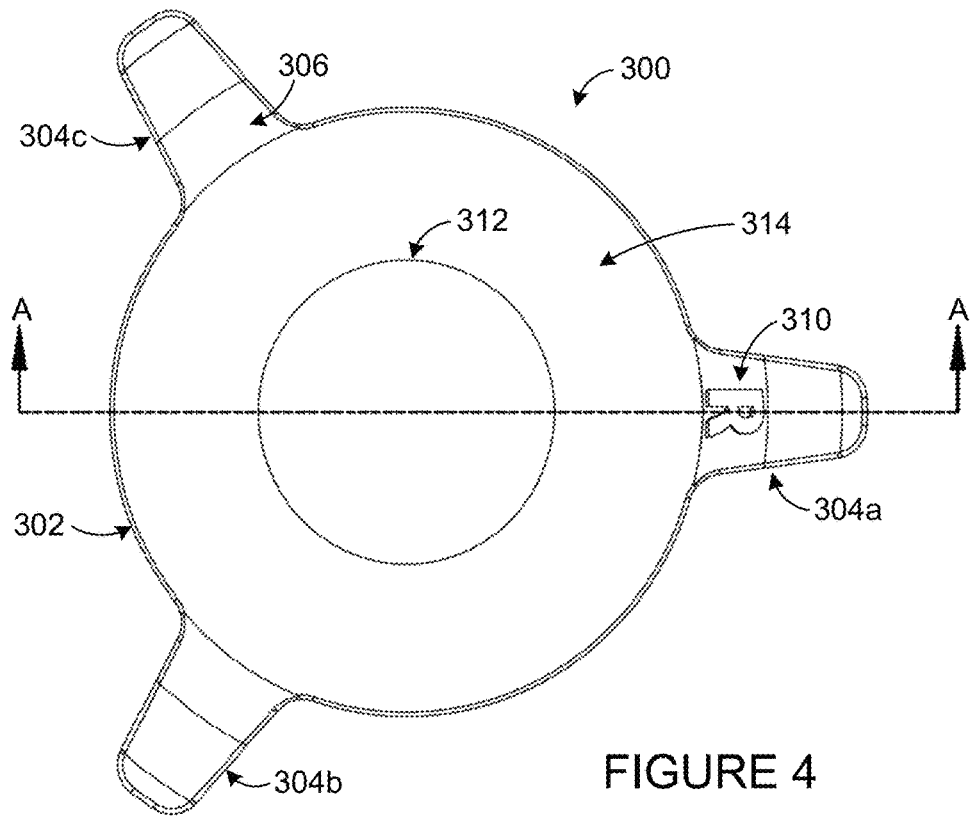
FIG. 4 illustrates a top view of an example intraocular pseudophakic contact lens for a Galilean vision system according to this disclosure.
Figure 5:
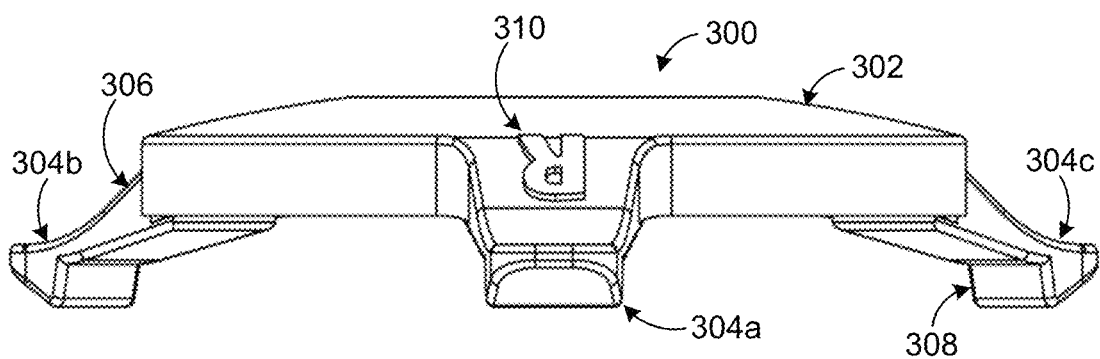
FIG. 5 illustrates a side view of an example intraocular pseudophakic contact lens for a Galilean vision system according to this disclosure.
Figure 6:
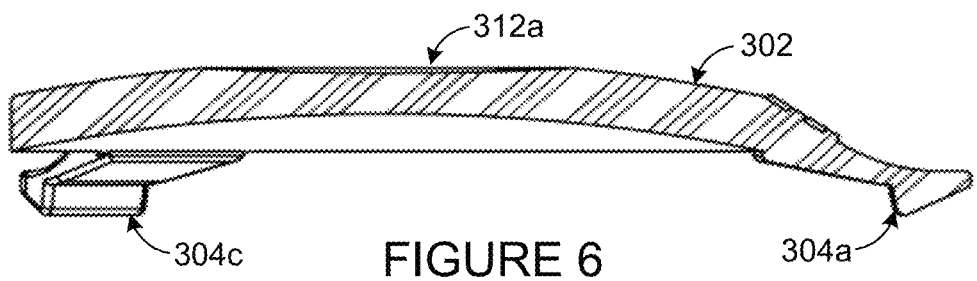
FIGS. 6 through 9 illustrate different cross-sectional views of an example intraocular pseudophakic contact lens for a Galilean vision system according to this disclosure.
Figure 7:
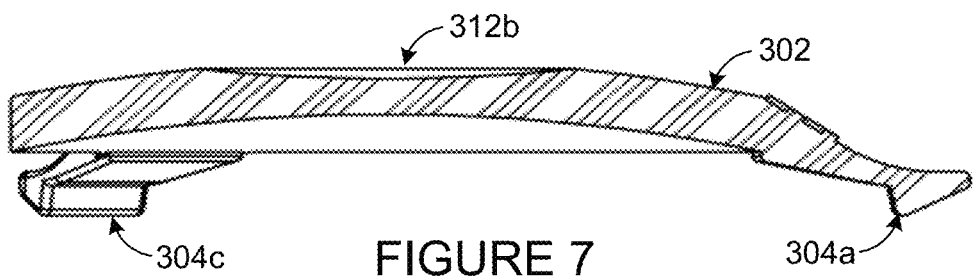
Figure 8:
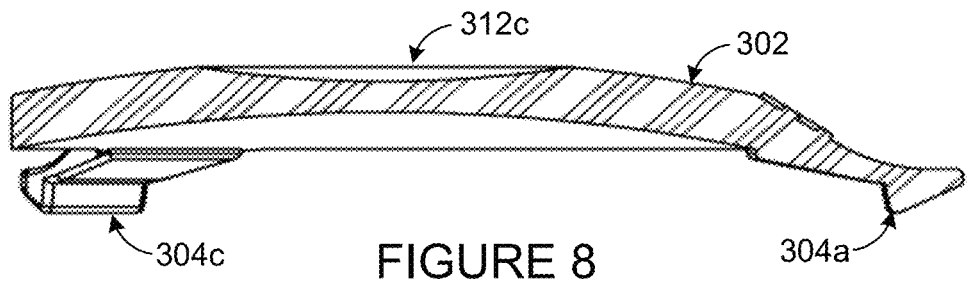
Figure 9:
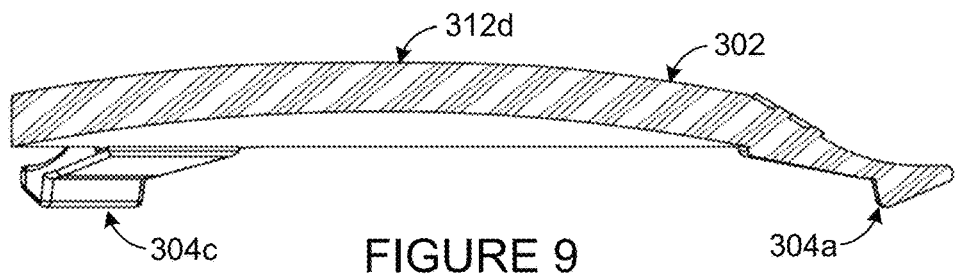

FIGS. 3 through 9 illustrate an example intraocular pseudophakic contact lens 300 for a Galilean vision system according to this disclosure. More specifically, FIG. 3 illustrates a perspective view of the intraocular pseudophakic contact lens 300, FIG. 4 illustrates a top view of the intraocular pseudophakic contact lens 300, and FIG. 5 illustrates a side view of the intraocular pseudophakic contact lens 300. FIGS. 6 through 9 illustrate different cross-sectional views of the intraocular pseudophakic contact lens 300. For ease of explanation, the intraocular pseudophakic contact lens 300 may be described as representing the intraocular pseudophakic contact lens 114 and as being used in the Galilean vision system 100 of FIGS. 1 and 2. However, the intraocular pseudophakic contact lens 300 may be used in any other suitable Galilean vision system, and the Galilean vision system may use any other suitable type of intraocular pseudophakic contact lens.

As shown in FIGS. 3 through 5, the intraocular pseudophakic contact lens 300 includes an optical lens 302, which denotes the portion of the intraocular pseudophakic contact lens 300 that alters light passing through the intraocular pseudophakic contact lens 300. For example, the light that passes through the optical lens 302 may then travel through an associated intraocular lens 112 before reaching the retina of a patient's eye 102. The optical lens 302 can be formed from any suitable material(s), such as silicone or acrylic. The optical lens 302 can also be formed in any suitable manner, such as by using a mold, laser, or lathe cut manufacturing process. Different optical lenses 302 in different intraocular pseudophakic contact lenses 300 can be designed and manufactured to provide different types of optical modifications, such as when different optical lenses 302 provide different high minus powers of optical magnification.

Multiple haptics 304a-304c extend from multiple sides of the optical lens 302. The haptics 304a-304c are sized and shaped so that they extend a short distance from the optical lens 302 and fit under the anterior leaflet of the capsular wall in a patient's eye 102 after implantation. Each haptic 304a-304c could be formed from any suitable material(s) and in any suitable manner. For example, each haptic 304a-304c could be formed from the same material(s) as the optical lens 302. Note that while three haptics 304a-304c are shown here, the intraocular pseudophakic contact lens 300 could include any number of haptics, including a single haptic. Also note that while the haptics 304a-304c angle downward (meaning the haptics 304a-304c generally extend outward and posteriorly from the optical lens 302), the haptics 304a-304c could have any other suitable arrangement. In addition, note that the haptics 304a-304c may be coupled to the optical lens 302 in any suitable manner, such as when the haptics 304a-304c are formed integral with the optical lens 302 or are attached to the optical lens 302 or to a retaining ring or other structure (integral with or attached to the optical lens 302) using adhesive or other suitable connecting mechanism.

Each of the haptics 304a-304c may include a textured surface 306, which may facilitate capture or confinement of the haptics 304a-304c by the anterior leaflet of the capsular wall in a patient's eye 102. Among other things, this can help the haptics 304a-304c to secure the intraocular pseudophakic contact lens 300 in place on or to the intraocular lens 112. In some cases, the textured surfaces 306 allow the haptics 304a-304c to actually physically bond to the anterior leaflet of the capsular wall in the patient's eye 102, such as through fibrosis or re-fibrosis during the healing process. In other cases, the textured surfaces 306 may simply resist movement of the haptics 304a-304c relative to the anterior leaflet of the capsular wall in the patient's eye 102.

Each textured surface 306 represents any suitable structure that facilitates confinement, capture, or attachment of the haptics 304a-304c by or to the anterior leaflet of the capsular wall. In some cases, each textured surface 306 may represent an electrical discharge machining (EDM) finish, or each textured surface 306 may represent holes formed partially or completely through the haptics 304a-304c (in which case the numbers and sizes of the holes in the textured surfaces 306 may vary as needed or desired). Note that other forms of texturing may be used here, or no texturing may be needed. Also note that the haptics 304a-304c may be omitted if not needed, such as when the intraocular pseudophakic contact lens 300 can be held in place on an intraocular lens 112 via surface tension, adhesive, or other technique. In addition, note that other types of haptics may be used with the intraocular pseudophakic contact lens 300, or pins embedded in or passing through projections from the optical lens of the intraocular pseudophakic contact lens 300 or other structures of the intraocular pseudophakic contact lens 300 may be used to secure the intraocular pseudophakic contact lens 300 to the intraocular lens 112. In general, this disclosure is not limited to any particular haptic design or mechanism for mounting or attaching the intraocular pseudophakic contact lens 300 on or to the intraocular lens 112.

In this example, the haptics 304a-304c of the intraocular pseudophakic contact lens 300 are formed as large projections that extend from the sides of the optical lens 302, effectively forming long "wings" extending from the optical lens 302. An inner portion of each haptic 304a-304c projects outward and downward (posteriorly) in this example, and an outer portion of each haptic 304a-304c projects outward and slightly upward in this example (although the outer portion of each haptic 304a-304c may be flexible as described below). Note, however, that other forms for the haptics 304a-304c could also be used. Each of the outer portions of the haptics 304a-304c has a thickness that tapers towards the outer edge of the haptic 304a-304c, which may facilitate easier insertion of the haptics 304a-304c under the anterior leaflet of the capsular wall in a patient's eye 102. The lower surfaces of the haptics 304a-304c also include ridges 308, and multiple ridges 308 of multiple haptics 304a-304c can be used to capture one or more edges of the underlying intraocular lens 112. This can help to center the intraocular pseudophakic contact lens 300 on the intraocular lens 112. This can also help to retain the intraocular pseudophakic contact lens 300 in place on the intraocular lens 112 during the healing process or otherwise during use. While the ridges 308 are shown here as being generally flat or slightly curved, the ridges 308 may incorporate other features. For instance, lips may be formed by small inward projections extending from the bottoms or other portion(s) of the ridges 308 inward towards a central optical axis of the optical lens 302 (meaning a vertical axis through the center of the optical lens 302 in FIG. 5).

The haptics 304a-304c may have any suitable positions in the intraocular pseudophakic contact lens 300. For example, in some embodiments, the haptics 304a-304c are evenly spaced about 120° apart. In other embodiments, the haptics 304a-304c are unevenly spaced, such as when the haptic 304a is separated from each of the haptics 304b-304c by about 125° and the haptics 304b-304c are separated from each other by about 110° (which may be based on, for instance, the positions of haptics of the intraocular lens 112 onto which the intraocular pseudophakic contact lens 300 will be placed). Also, in some cases, the intraocular pseudophakic contact lens 300 may be designed for implantation into a patient's eye 102 at a specific orientation, and at least one alignment marking 310 may be provided to identify proper orientation of the intraocular pseudophakic contact lens 300 in the eye 102. In this example, a single alignment marking 310 having the form of a raised letter "R" may be used, such as to identify the haptic 304a to be positioned on the right side of the intraocular lens 112 as the intraocular lens 112 within the eye 102 is viewed by a surgeon or other personnel. However, any other or additional alignment markings 310 or no alignment markings may be used here.

The optical lens 302 may have any suitable optical power(s) depending on the implementation. In this example, the optical lens 302 includes a first lens portion 312 and a second lens portion 314, where the two portions 312-314 of the optical lens 302 may provide different levels of optical magnification. For instance, the first lens portion 312 may provide a specified amount of magnification (such as a high minus power magnification), and the second lens portion 314 may provide a different amount of magnification or possibly little or no magnification. To provide a high minus power in this example, the anterior surface of the first lens portion 312 may be convex or concave, and the posterior surface of the first lens portion 312 may be concave. The amount of high minus power magnification can be adjusted here by altering the shape of one or more of the anterior and posterior surfaces of the first lens portion 312. For instance, FIGS. 6 through 9 illustrate example cross-sections of the intraocular pseudophakic contact lens 300 taken along line A-A in FIG. 4, where different first lens portions 312a-312d are shown as having different shapes in their anterior surfaces. These different shapes allow the different first lens portions 312a-312d to provide different amounts of high minus power magnification. As a particular example, the lens portion 312a may provide an optical power of −15 diopters, the lens portion 312b may provide an optical power of −20 diopters, the lens portion 312c may provide an optical power of −25 diopters, and the lens portion 312d may provide an optical power of −5 diopters (although these are example values only).

As a result, the first lens portion 312 in the intraocular pseudophakic contact lens 300 can be used to provide a high amount of minus power optical magnification. This supports the use of the intraocular pseudophakic contact lens 300 in the Galilean vision system 100, where the external lens 116 can provide a high amount of plus power optical magnification. The second lens portion 314 in the intraocular pseudophakic contact lens 300 can be used to provide a different amount of optical magnification or no optical magnification. For instance, the anterior surface of the second lens portion 314 may be convex, and the posterior surface of the second lens portion 314 may be concave. Thus, the central segment of the optical lens 302 shown here can be used to increase a field of vision, such as to intermediate or near. This can be used to help treat conditions such as AMD or other vision loss related to retinal disease.

In this particular example, the first lens portion 312 is generally circular and positioned centrally in the intraocular pseudophakic contact lens 300, and the second lens portion 314 is generally annular and surrounds the first lens portion 312. However, each lens portion 312 and 314 may have any other suitable size, shape, and position within the intraocular pseudophakic contact lens 300. In general, the sizes, shapes, and positions of the lens portions 312-314 can vary as needed or desired in order to provide the desired optical magnification(s).

The intraocular pseudophakic contact lens 300 shown in FIGS. 3 through 9 can be easily secured over an intraocular lens 112, such as by capturing and confining the haptics 304a-304c of the intraocular pseudophakic contact lens 300 using the anterior leaflet of the capsular wall in the eye 102. In some cases, this could also involve physical bonding of the haptics 304a-304c to the anterior leaflet of the capsular wall, such as via a fibrosis or re-fibrosis mechanism. Thus, in some embodiments, the intraocular pseudophakic contact lens 300 may not need to be designed to work specifically with particular structures of any specific intraocular lenses 112. Instead, the intraocular lens 112 being used with an intraocular pseudophakic contact lens 300 need not have any predefined structures that are provided for coupling to an intraocular pseudophakic contact lens 300. Rather, the intraocular pseudophakic contact lens 300 can simply be sized so that, when the intraocular pseudophakic contact lens 300 is placed on the intraocular lens 112, it can be secured in place through capture and confinement by (and possibly bonding with) the anterior leaflet of the capsular wall. This allows the intraocular pseudophakic contact lens 300 to be used with a wide variety of intraocular lenses 112, including different types of intraocular lenses 112 and including existing intraocular lenses 112 already implanted into patients. There is no need to remove an existing intraocular lens 112 from a patient in order to install a new intraocular lens and an intraocular pseudophakic contact lens. Note, however, that an intraocular pseudophakic contact lens may also be designed to specifically mate with a particular intraocular lens in other embodiments.

Moreover, the intraocular pseudophakic contact lens 300 could be easily removed from a patient's eyes 102, such as any suitable time after implantation or prior to bonding of the haptics 304a-304c to the capsular wall (assuming fibrosis or re-fibrosis holds the intraocular pseudophakic contact lens 300 in place). Among other things, this allows one intraocular pseudophakic contact lens 300 to be removed and replaced with a different intraocular pseudophakic contact lens 300 if a different optical magnification is needed or desired.

The intraocular pseudophakic contact lens 300 could have any suitable size, shape, and dimensions. For example, intraocular pseudophakic contact lenses 300 could be made available in a range of diameters from about 4 millimeters to about 6 millimeters. Also, the intraocular pseudophakic contact lenses 300 could be made available with varying base curvatures for their optical lenses 302. Of course, an intraocular pseudophakic contact lens 300 could also be custom designed for a particular patient's eye 102, such as when one or more specific curvatures are needed to provide a desired amount of optical magnification in the particular patient's eye 102.

In some embodiments, the intraocular pseudophakic contact lens 300 and various components of the intraocular pseudophakic contact lens 300 may have the following design parameters. The diameter of the first lens portion 312 may be about 2.25 millimeters, the diameter of the second lens portion 314 may be about 4.5 millimeters, the diameter of a circle defined by the ridges 308 may be about 6.05 millimeters, and the diameter of a circle defined by outer edges of the haptics 304a-304c may be about 7 millimeters. The straight edges of each haptic 304a-304c when viewed from the top may taper from a separation of about 0.97 millimeters to about 0.63 millimeters, where the straight edges define an angle of about 15°. The optical lens 302 may have a thickness along its outer edge of about 0.375 millimeters, and there may be a step of about 0.065 millimeters between the posterior surface of the optical lens 302 along its outer edge and posterior surfaces of the haptics 304a-304c. Each of the ridges 308 may form an angle of about 10° relative to a central optical axis of the optical lens 302, and the posterior surfaces of the haptics 304a-304c may extend from the optical lens 302 at an angle of about 103° relative to the central optical axis of the optical lens 302. The distance between the ridge 308 and the outer edge of each haptics 304a-304c may be about 0.48 millimeters. Various corners and edges of the intraocular pseudophakic contact lens 300 can be rounded, and the radii of curvatures of the anterior and posterior surfaces of the first and second lens portions 312-314 can vary based on the desired optical magnification(s) to be provided by the lens portions 312-314. Note, however, that these dimensions and other design parameters are for illustration only and can vary as needed or desired depending on the implementation of the intraocular pseudophakic contact lens 300.

The intraocular pseudophakic contact lens 300 can be implanted non-invasively in a patient's eye 102 and easily positioned on an intraocular lens 112. The implantation is non-invasive because the intraocular pseudophakic contact lens 300 is being installed on the anterior surface of an intraocular lens 112, which is typically easily accessible by a surgeon or other personnel during an implantation procedure. The implantation is also non-invasive because the intraocular pseudophakic contact lens 300 can be attached to the intraocular lens 112 without requiring attachment of the intraocular pseudophakic contact lens 300 to anatomical structures within the patient's eye 102, such as to the sulcus of the patient's eye 102. The non-invasive implantation and easy positioning of an intraocular pseudophakic contact lens 300 provide a safe and effective surgical procedure to correct AMD or other eye disorders.

If the haptics 304a-304c of the intraocular pseudophakic contact lens 300 include ridges 308, the ridges 308 can be used to center the intraocular pseudophakic contact lens 300 on an underlying intraocular lens 112 as described above. If the intraocular pseudophakic contact lens 300 includes multiple haptics 304a-304c with associated ridges 308, the ridges 308 could help to perfectly center the intraocular pseudophakic contact lens 300 on the underlying intraocular lens 112. Such an approach allows the ridges 308 of the intraocular pseudophakic contact lens' haptics 304a-304c to capture the underlying intraocular lens 112 at the edge and perfectly line up the optical center of the intraocular pseudophakic contact lens' optic with the optical center of the intraocular lens 112. This alignment helps to reduce or avoid induced optical aberrations or induced prisms caused by optical center misalignment.

Note that in the above example, the intraocular pseudophakic contact lens 300 could possibly be designed so that only the haptics 304a-304c of the intraocular pseudophakic contact lens 300 extend under the anterior leaflet of the capsular wall in a patient's eye 102. This allows the haptics 304a-304c to be captured and confined by the anterior leaflet while leaving the optical lens 302 of the intraocular pseudophakic contact lens 300 free and generally unobscured by the surrounding tissue in the patient's eye 102.

Also note that, in some embodiments, the surgical tool disclosed in U.S. Patent Application Publication No. 2019/0269555 A1 (which is hereby incorporated by reference in its entirety) may be used to help implant an intraocular pseudophakic contact lens 300. For example, this tool may be used to separate at least part of the anterior leaflet of a patient's eye 102 from an implanted intraocular lens 112, allowing haptics 304a-304c of the intraocular pseudophakic contact lens 300 to be inserted between the anterior leaflet and the intraocular lens 112. As another example, this tool may be used to separate the anterior leaflet of a patient's eye 102 from an implanted intraocular pseudophakic contact lens, allowing the intraocular pseudophakic contact lens to be removed (and possibly replaced).

Although FIGS. 3 through 9 illustrate one example of an intraocular pseudophakic contact lens 300 for a Galilean vision system 100, various changes may be made to FIGS. 3 through 9. For example, the intraocular pseudophakic contact lens 300 could include any suitable number of each component shown in the figures. As a particular example, while the optical lens 302 is shown as having two portions 312 and 314, the optical lens 302 may have more than two regions (such as two or more annular regions around the central region). Also, the forms of the haptics 304a-304c shown here are examples only, and any other suitable structures or other mechanisms could be used to secure the intraocular pseudophakic contact lens 300 in place. Further, a number of other features could be used at one or more locations of the intraocular pseudophakic contact lenses 300. For instance, one or more drug-eluting materials could be placed on top, side, or bottom surfaces of the optical lenses in the intraocular pseudophakic contact lenses. Moreover, the specific dimensions, diopters, optical powers, and other values described above are for illustration only and do not limit this disclosure to the specific values.

In addition, the intraocular pseudophakic contact lens 300 shown in FIGS. 3 through 9 represents one example of the type of intraocular device that may be designed or modified for use in the Galilean vision system 100. However, various other intraocular devices may be designed or modified for use in the Galilean vision system 100. For example, U.S. Patent Application Publication No. 2020/0121446 A1 and U.S. Patent Application Publication No. 2019/0076237 A1 (both of which are hereby incorporated by reference in their entirety) disclose a number of intraocular pseudophakic contact lenses that may be modified to include optical lenses providing a central high minus power optical magnification, which would allow those intraocular pseudophakic contact lenses to be used in the Galilean vision system 100. Among other things, the intraocular pseudophakic contact lenses disclosed in the documents incorporated by reference above use pins, haptic loops, or other structures to secure the intraocular pseudophakic contact lenses to intraocular lenses, and any of these structures may be used with an intraocular pseudophakic contact lens in a Galilean vision system.

Figure 10:
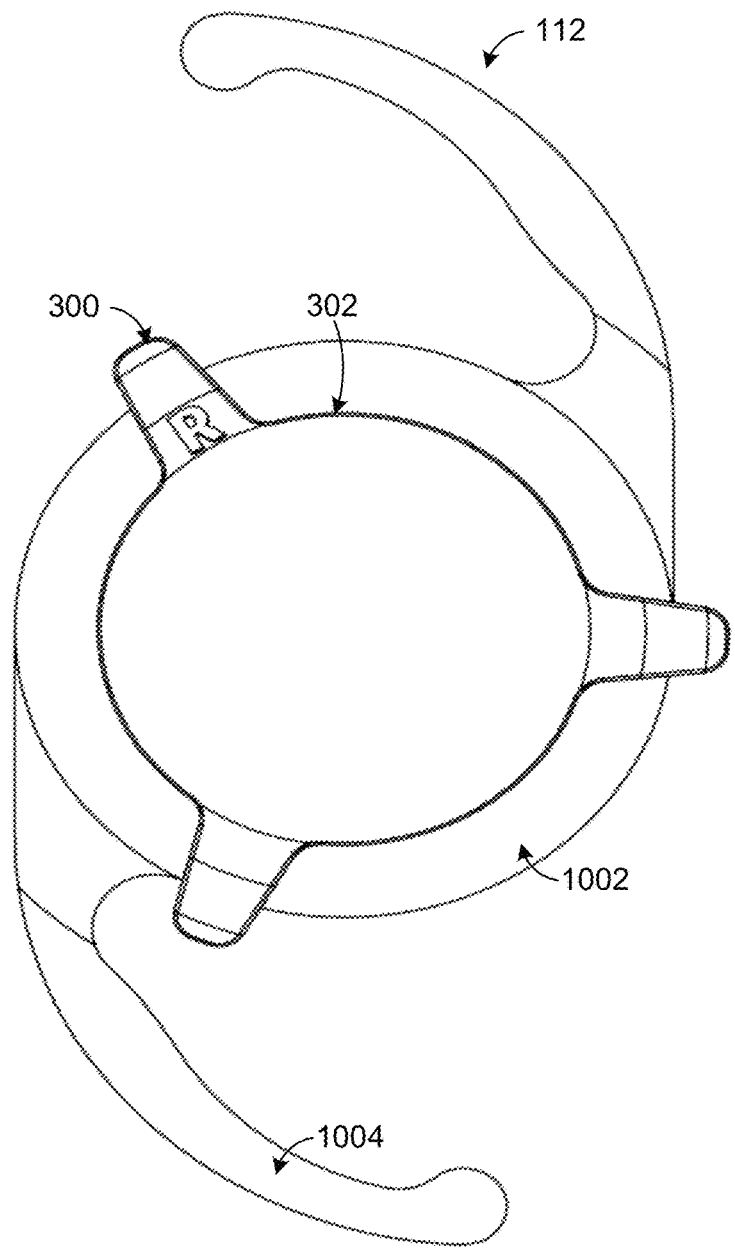
FIGS. 10 and 11 illustrate an example combination of an intraocular pseudophakic contact lens and an artificial intraocular lens that may be used in a Galilean vision system according to this disclosure.
Figure 11:
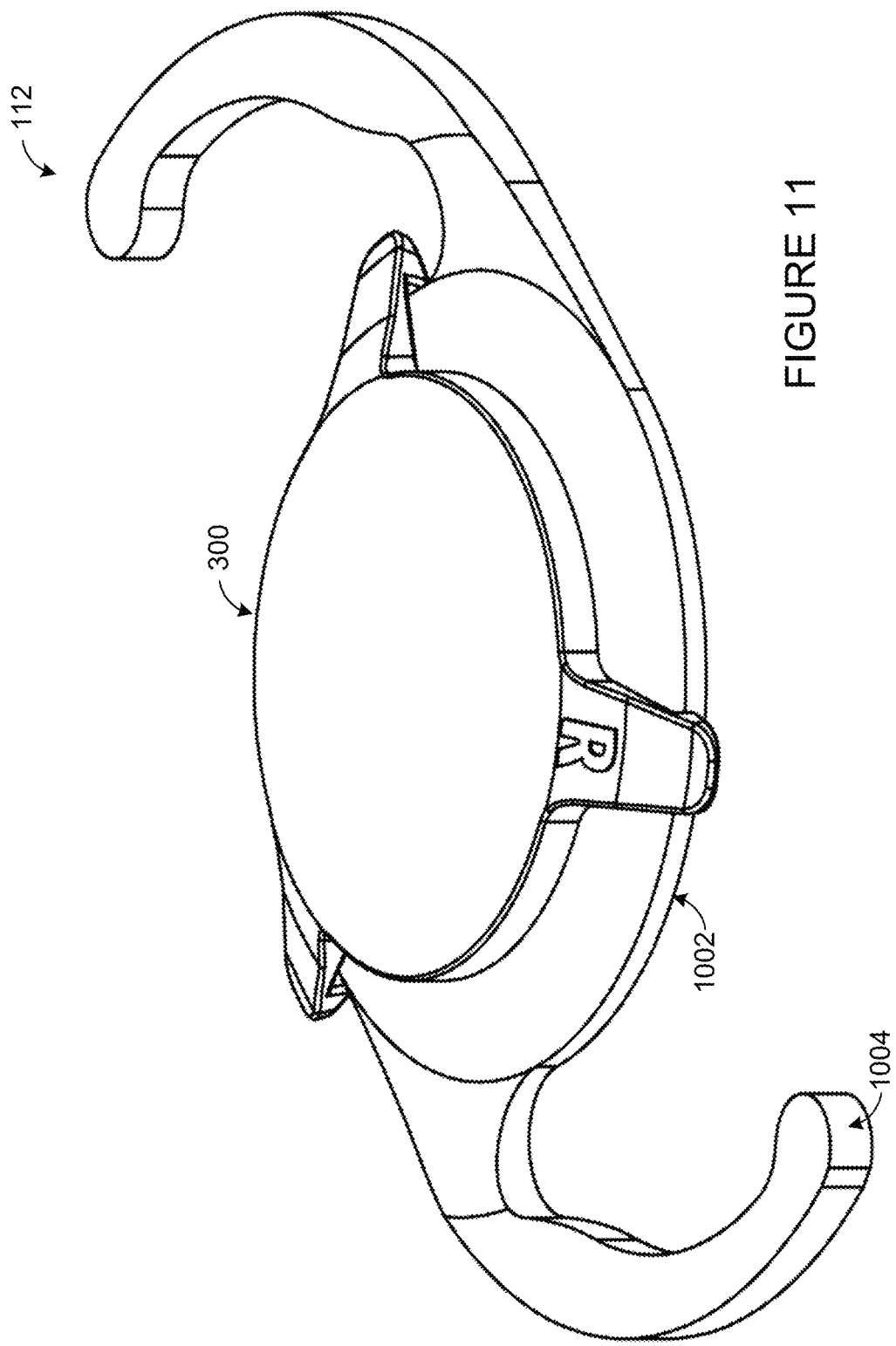

FIGS. 10 and 11 illustrate an example combination of an intraocular pseudophakic contact lens 300 and an artificial intraocular lens 112 that may be used in a Galilean vision system according to this disclosure. For ease of explanation, the combination may be described as being used in the Galilean vision system 100 of FIGS. 1 and 2. However, the combination may be used in any other suitable Galilean vision system, and the Galilean vision system may use any other suitable combination of an intraocular pseudophakic contact lens and an intraocular lens.

As shown in FIGS. 10 and 11, the intraocular lens 112 includes an optical lens 1002 and haptics 1004 extending from the optical lens 1002. The optical lens 1002 receives light that has passed through the optical lens 302 of the intraocular pseudophakic contact lens 300 and focuses the light onto the retina of the eye 102. The haptics 1004 help to hold the intraocular lens 112 within the capsular bag 110 so that the optical lens 1002 is in a desired position within the eye 102. Note that the forms of the optical lens 1002 and the haptics 1004 shown here are examples only and that other intraocular lens may include different optical lenses or different haptics.

Figure 12:
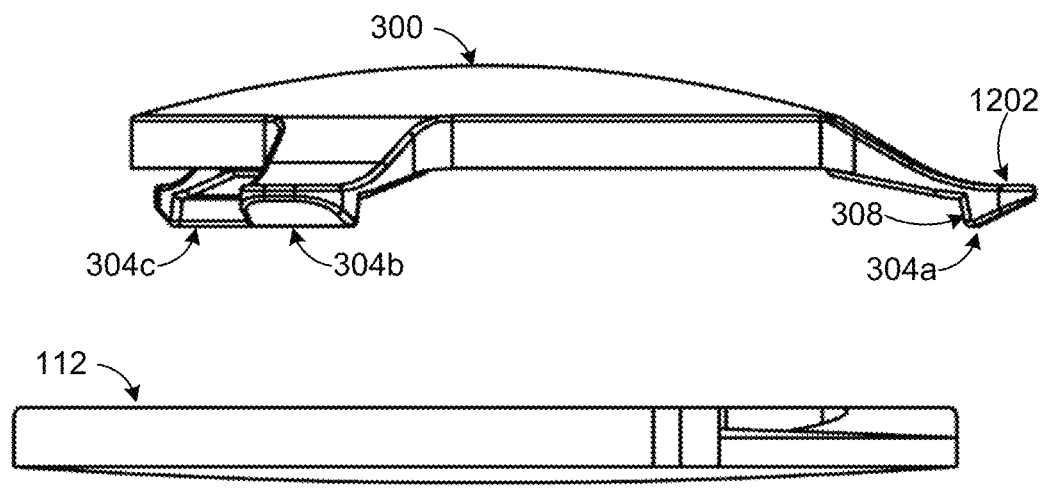
FIGS. 12 through 14 illustrate an example coupling of an intraocular pseudophakic contact lens to an artificial intraocular lens for use in a Galilean vision system according to this disclosure.
Figure 13:
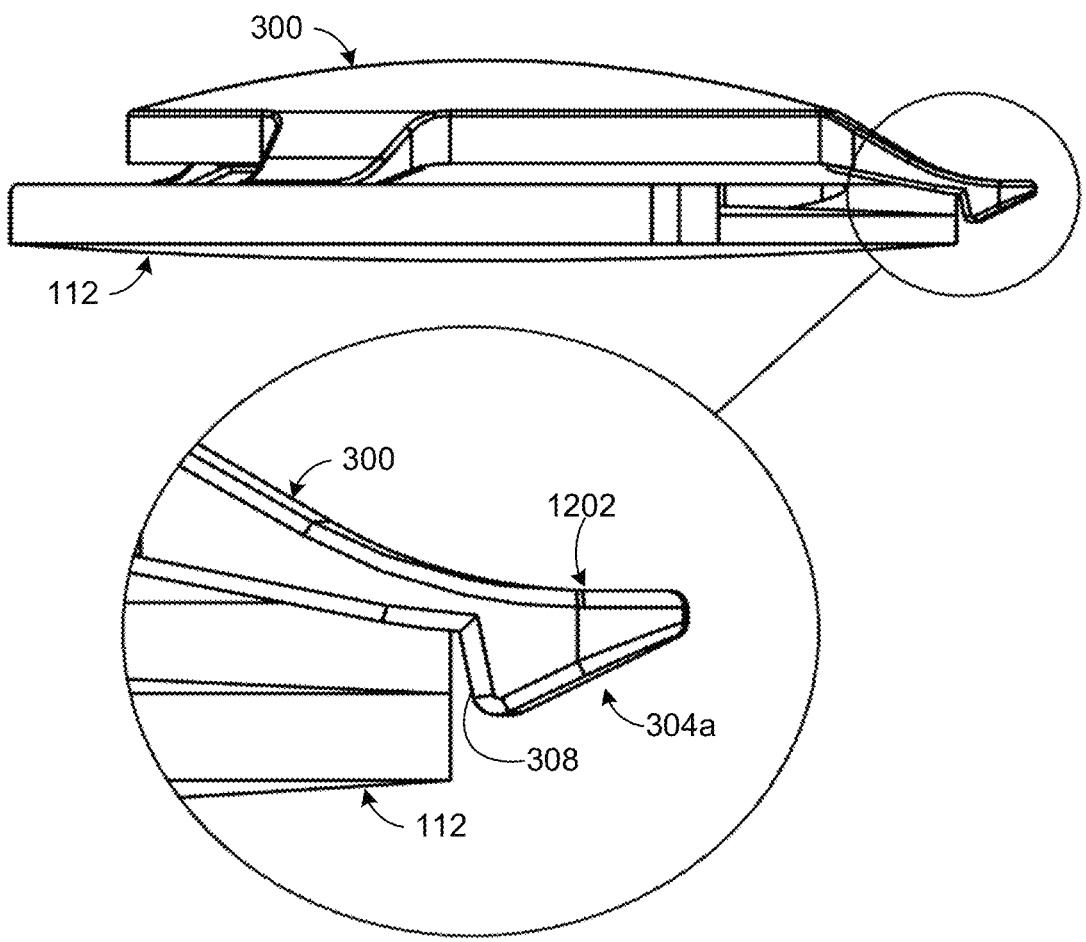
Figure 14:
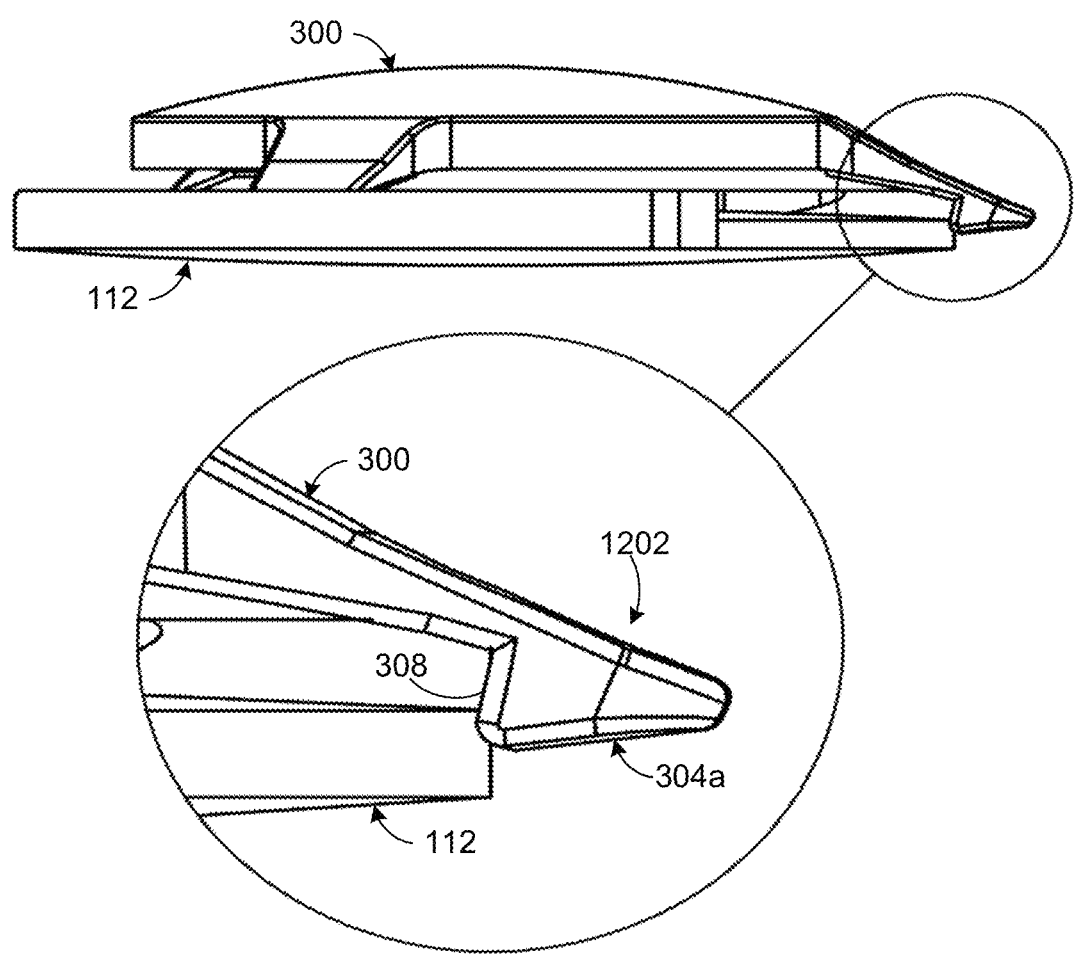

FIGS. 12 through 14 illustrate an example coupling of the intraocular pseudophakic contact lens 300 to the artificial intraocular lens 112 for use in a Galilean vision system according to this disclosure. For ease of explanation, the coupling may be described as being performed to help form the Galilean vision system 100 of FIGS. 1 and 2. However, the coupling may involve any other suitable Galilean vision system, and the Galilean vision system may use any other suitable coupling of an intraocular pseudophakic contact lens and an intraocular lens.

As shown in FIG. 12, the intraocular pseudophakic contact lens 300 and the intraocular lens 112 are shown in side profile, and the intraocular pseudophakic contact lens 300 is being moved towards the intraocular lens 112. An outer portion 1202 of each haptic 304a-304c angles partially upward here, which facilitates coupling of the intraocular pseudophakic contact lens 300 to the intraocular lens 112 as described below. The intraocular pseudophakic contact lens 300 can be moved towards the intraocular lens 112 in any suitable manner, such as when a surgeon or other personnel uses a tool to grasp and manipulate the intraocular pseudophakic contact lens 300.

As shown in FIG. 13, the intraocular pseudophakic contact lens 300 is being placed onto the anterior surface of the intraocular lens 112. However, in FIG. 13, it is assumed that the outer portions 1202 of the haptics 304a-304c have not been placed under the anterior leaflet in the eye 102, which is why the outer portions 1202 of the haptics 304a-304c still angle partially upward here. This allows the ridges 308 of the haptics 304a-304c to more easily surround and capture the outer edge of the optical lens 1002 of the intraocular lens 112.

As shown in FIG. 14, the intraocular pseudophakic contact lens 300 has now been secured to the anterior surface of the intraocular lens 112. In FIG. 14, it is assumed that the outer portions 1202 of the haptics 304a-304c have been placed under the anterior leaflet in the eye 102. The anterior leaflet applies a downward force to the outer portions 1202 of the haptics 304a-304c. Assuming the haptics 304a-304c are flexible, this surface pressure causes the outer portions 1202 of the haptics 304a-304c to deflect and angle partially downward, which helps to drive the ridges 308 (and optionally any lips or other structures on the ridges 308) into the outer edge of the optical lens 1002 of the intraocular lens 112. This helps to secure the intraocular pseudophakic contact lens 300 to the intraocular lens 112 and helps to align the optical axes of the intraocular pseudophakic contact lens 300 and the intraocular lens 112.

Although FIGS. 10 and 11 illustrate one example of a combination of an intraocular pseudophakic contact lens 300 and an artificial intraocular lens 112 that may be used in a Galilean vision system 100 and FIGS. 12 through 14 illustrate one example of a coupling of an intraocular pseudophakic contact lens 300 to an artificial intraocular lens 112 for use in a Galilean vision system 100, various changes may be made to FIGS. 10 through 14. For example, any other suitable mechanism (possibly including just surface tension) may be used to hold the intraocular pseudophakic contact lens on or against the intraocular lens.

Figure 15:
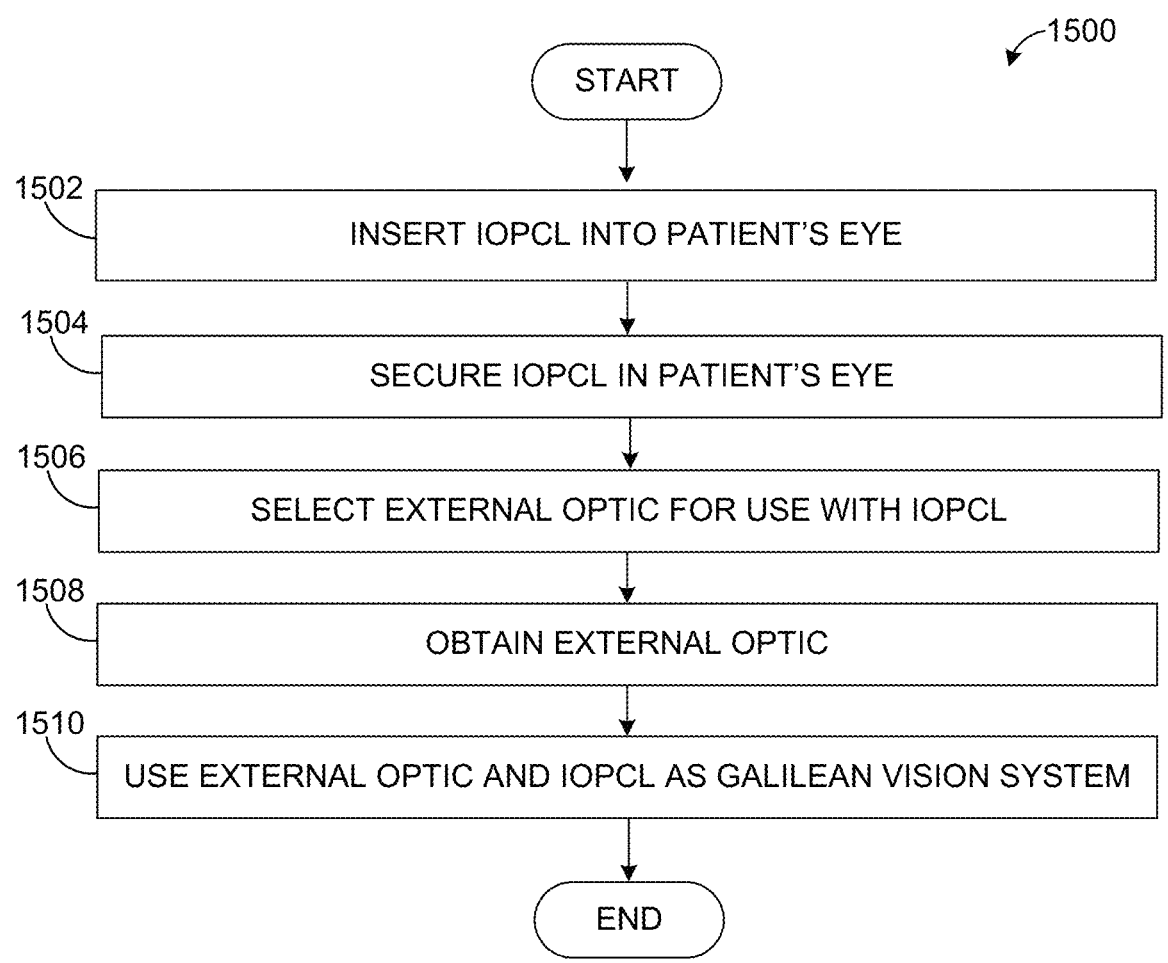
FIG. 15 illustrates an example method for forming a Galilean vision system according to this disclosure.

FIG. 15 illustrates an example method 1500 for forming a Galilean vision system according to this disclosure. For ease of explanation, the method 1500 is described as using the intraocular pseudophakic contact lens 300 and the external lens 116 as part of the formation of the Galilean vision system 100. However, the method 1500 may use any other suitable intraocular pseudophakic contact lens and any other suitable external lens and may form any other suitable Galilean vision system.

As shown in FIG. 15, an intraocular pseudophakic contact lens (IOPCL) is inserted into a patient's eye at step 1502 and secured in the patient's eye at step 1504. This may include, for example, a surgeon or other personnel selecting an intraocular pseudophakic contact lens 300 that provides a desired amount of high minus power optical magnification, such as from a kit. This may also include the surgeon or other personnel forming a small incision in the patient's eye 102 and inserting the intraocular pseudophakic contact lens 300 into the eye 102 through the incision. The intraocular pseudophakic contact lens 300 can be rolled, folded, or otherwise reduced in cross-sectional size in order to insert the intraocular pseudophakic contact lens 300 through a smaller incision. This may further include one or more haptics 304a-304c of the intraocular pseudophakic contact lens 300 sliding or otherwise being inserted under the anterior leaflet of the capsular wall in the patient's eye 102.

An external optic is selected for use with the intraocular pseudophakic contact lens at step 1506 and obtained at step 1508. This may include, for example, a surgeon or other personnel selecting a suitable external lens 116 that provides a desired amount of high plus power optical magnification. This may also include the surgeon or other personnel forming the external lens 116 or the patient otherwise obtaining the external lens 116 having the desired amount of high plus power optical magnification. The intraocular pseudophakic contact lens and the external optic are used as a Galilean vision system at step 1510. This may include, for example, the patient wearing the external lens 116 (which acts as the objective lens of the Galilean vision system) while having the implanted intraocular pseudophakic contact lens 300 (which acts as the eyepiece of the Galilean vision system).

Although FIG. 15 illustrates one example of a method 1500 for forming a Galilean vision system 100, various changes may be made to FIG. 15. For example, while shown as a series of steps, various steps in FIG. 15 could overlap, occur in parallel, occur in a different order, or occur any number of times.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in this patent document should not be read as implying that any particular element, step, or function is an essential or critical element that must be included in the claim scope. Also, none of the claims is intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," "processing device," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system comprising:
   an intraocular pseudophakic contact lens configured to be implanted in an eye and mounted on or attached to an artificial intraocular lens in the eye; and
   an external lens configured to be positioned in front of the eye;
   wherein the intraocular pseudophakic contact lens and the external lens form a telescopic Galilean vision system;
   wherein the intraocular pseudophakic contact lens comprises (i) an optical lens and (ii) haptics extending radially from the optical lens and configured to be inserted under an anterior leaflet of a capsular wall in the eye;
   wherein posterior surfaces of the haptics comprise ridges configured to capture at least one edge of the artificial intraocular lens; and
   wherein the haptics are flexible such that outer portions of the haptics are configured to drive the ridges into the at least one edge of the artificial intraocular lens based on surface pressure from the anterior leaflet against the outer portions of the haptics.

2. The system of claim 1, wherein the external lens comprises one of: a spectacle lens and a contact lens.

3. The system of claim 1, wherein:
   the optical lens is configured to provide a minus power optical magnification; and
   the external lens is configured to provide a plus power optical magnification.

4. The system of claim 3, wherein the optical lens of the intraocular pseudophakic contact lens is configured to provide an optical power of about −5 diopters to about −25 diopters.

5. The system of claim 1, wherein anterior surfaces of the haptics are configured to contact an inner capsular wall surface at the anterior leaflet, the anterior surfaces of the haptics comprising textured surfaces.

6. The system of claim 1, wherein:
   the optical lens comprises a central portion configured to provide a minus power optical magnification; and
   the optical lens further comprises an annular portion surrounding the central portion and configured to provide a different power optical magnification or no optical magnification.

7. The system of claim 6, wherein:
   the central portion of the optical lens comprises a convex or concave anterior surface and a concave posterior surface; and the annular portion of the optical lens comprises a convex anterior surface and a concave posterior surface.

8. The system of claim 1, wherein:
the ridges angle outwards prior to placement of the outer portions of the haptics under the anterior leaflet; and
the haptics being flexible allows the ridges to angle inwards in response to the surface pressure from the anterior leaflet against the outer portions of the haptics.

9. The system of claim 1, wherein:
the ridge of each haptic is defined where a larger thickness of the outer portion of the haptic meets a smaller thickness of an inner portion of the haptic; and
the haptics being flexible allows the outer portion of each haptic to angle upward prior to placement of the outer portion of the haptic under the anterior leaflet.

10. The system of claim 9, wherein the haptics being flexible allows the surface pressure from the anterior leaflet against the outer portions of the haptics to push the outer portions of the haptics downward.

11. A method comprising:
using an intraocular pseudophakic contact lens and an external lens to form a telescopic Galilean vision system;
wherein the intraocular pseudophakic contact lens is configured to be implanted in an eye and mounted on or attached to an artificial intraocular lens in the eye;
wherein the external lens is configured to be positioned in front of the eye;
wherein the intraocular pseudophakic contact lens comprises (i) an optical lens and (ii) haptics extending radially from the optical lens and configured to be inserted under an anterior leaflet of a capsular wall in the eye;
wherein posterior surfaces of the haptics comprise ridges configured to capture at least one edge of the artificial intraocular lens; and
wherein the haptics are flexible such that outer portions of the haptics are configured to drive the ridges into the at least one edge of the artificial intraocular lens based on surface pressure from the anterior leaflet against the outer portions of the haptics.

12. The method of claim 11, wherein the external lens comprises one of: a spectacle lens and a contact lens.

13. The method of claim 11, wherein:
the optical lens is configured to provide a minus power optical magnification; and
the external lens is configured to provide a plus power optical magnification.

14. The method of claim 13, wherein:
the external lens functions as an objective lens in the telescopic Galilean vision system; and
the optical lens of the intraocular pseudophakic contact lens functions as an eyepiece in the telescopic Galilean vision system.

15. The method of claim 11, wherein:
the optical lens comprises a central portion configured to provide a minus power optical magnification; and
the optical lens further comprises an annular portion surrounding the central portion and configured to provide a different power optical magnification or no optical magnification.

16. The method of claim 15, wherein:
the central portion of the optical lens comprises a convex or concave anterior surface and a concave posterior surface; and
the annular portion of the optical lens comprises a convex anterior surface and a concave posterior surface.

17. The method of claim 11, wherein:
the ridges angle outwards prior to placement of the outer portions of the haptics under the anterior leaflet; and
the haptics being flexible allows the ridges to angle inwards in response to the surface pressure from the anterior leaflet against the outer portions of the haptics.

18. The method of claim 11, wherein:
the ridge of each haptic is defined where a larger thickness of the outer portion of the haptic meets a smaller thickness of an inner portion of the haptic; and
the haptics being flexible allows the outer portion of each haptic to angle upward prior to placement of the outer portion of the haptic under the anterior leaflet.

19. The method of claim 18, wherein the haptics being flexible allows the surface pressure from the anterior leaflet against the outer portions of the haptics to push the outer portions of the haptics downward.

20. A system comprising:
an intraocular pseudophakic contact lens configured to be implanted in an eye and mounted on or attached to an artificial intraocular lens in the eye; and
an external lens configured to be positioned in front of the eye, the external lens comprising one of: a spectacle lens and a contact lens;
wherein the intraocular pseudophakic contact lens and the external lens form a telescopic Galilean vision system;
wherein the intraocular pseudophakic contact lens comprises (i) an optical lens and (ii) haptics extending radially from the optical lens and configured to be inserted under an anterior leaflet of a capsular wall in the eye;
wherein the optical lens of the intraocular pseudophakic contact lens is configured to provide a minus power optical magnification;
wherein the external lens is configured to provide a plus power optical magnification;
wherein posterior surfaces of the haptics comprise ridges configured to capture at least one edge of the artificial intraocular lens; and
wherein the haptics are flexible such that outer portions of the haptics are configured to drive the ridges into the at least one edge of the artificial intraocular lens based on surface pressure from the anterior leaflet against the outer portions of the haptics.

* * * * *